United States Patent [19]

Lorenzoni et al.

[11] Patent Number: 5,047,587

[45] Date of Patent: Sep. 10, 1991

[54] PROCESS FOR PURIFYING OXALIC ACID DIAMIDE

[75] Inventors: Loreno Lorenzoni, Porto Torres; Giuseppe Messina, Alghero; Vittorio Bruzzi, Milan, all of Italy

[73] Assignee: Enichem Anic S.p.A., Palermo, Italy

[21] Appl. No.: 129,843

[22] Filed: Dec. 8, 1987

[30] Foreign Application Priority Data

Dec. 11, 1986 [IT] Italy ............................... 22638 A/86

[51] Int. Cl.$^5$ ...................... C07B 63/00; C07C 103/4
[52] U.S. Cl. .................................... 564/160; 564/125
[58] Field of Search ............... 564/160, 125, 206, 216

[56] References Cited

U.S. PATENT DOCUMENTS 3,776,957 12/1973 Newkirk ............................ 564/206
3,989,753 11/1976 Riemenschneider et al. ...... 564/125

FOREIGN PATENT DOCUMENTS 2423538 11/1975 Fed. Rep. of Germany ...... 564/160
2427269 12/1975 Fed. Rep. of Germany ...... 564/160
51-29430  3/1976 Japan ................................... 564/125
59-36647  2/1984 Japan ................................... 564/160
59-39858  3/1984 Japan ................................... 564/160

*Primary Examiner*—Carolyn Elmore
*Attorney, Agent, or Firm*—Hedman, Gibson, Costigan & Hoare

[57] ABSTRACT

A process is disclosed for the purification of the diamide of oxalic acid obtained by means a process wherein copper catalysts are used, by means of the washing with aqueous solutions of an ammonium salt of an organic or inorganic acid, operating at a pH value comprised within the range of from 2 to 8, and at a temperature comprised within the range of from 40° to 150° C.

10 Claims, No Drawings

PROCESS FOR PURIFYING OXALIC ACID DIAMIDE

The present invention relates to a process for purifying the diamide of oxalic acid, obtained by means of a process wherein copper catalysts are used.

The diamide of oxalic acid, or oxamide, is a product which finds several applications in many branches of chemistry, both as a finished product, and as an intermediate. It is in fact commonly used in agriculture, as a delayed-release fertilizer, and as an additive for fodder, in the fields of plastics materials and of paints, as a stabilizer, and as an intermediate for several other products, such as, e.g., diacetyl-oxamide, used in the sector of detergents.

The large-scale usage of oxamide has anyway only become possible from an economic standpoint, approximately ten years ago, or so, with the introduction of the so-said "Hoechst process". Up to that date, in fact, oxamide was synthetized by oxidating HCN with $H_2O_2$, or with $NO_2$.

Apart from the considerable cost of the oxidating agents which were then used, and the problems of the separation of the end product, in both said cases the synthesis had to be carried out as two separate steps, firstly isolating the intermediate cyanogen, and then reacting this intermediate with water, to yield oxamide; said two-step route rendered the synthesis not much suitable for being run at an industrial level.

The Hoechst process, which practically consists in the catalytic oxidation of hydrogen cyanide with air and oxygen, using a catalyst constituted by copper salts dissolved in acetic acid, makes it possible oxamide to be obtained, on the contrary, in one step only, and with nearly quantitative yields.

But this process suffers from the drawback that it leads to the production of an oxamide containing from 500 to 500 ppm of copper, whose presence, besides giving the product an undesired colour, makes it unacceptable for some commercial uses.

The copper present in the oxamide as produced according to this process is however bonded in such a stable way, that even after repeated washings with water, or other solvents, it is practically impossible to obtain an adequate removal thereof.

Among the conventional methods tested in order to obviate this problem, also the recrystallization of oxamide was taken into consideration, which, besides considerably decreasing the product yields, also showed to be very problematical, due to the poor solubility of oxamide in most of commonly used solvents.

The present Applicant has now surprisingly found, and this is the object of the present invention, that it is possible to obtain the nearly complete removal of copper from oxamide, by contacting this latter with an aqueous solution of a complexing agent for copper, constituted by an ammonium salt of an organic or inorganic acid, and operating at a pH value comprised within the range of from 2 to 8, and at a temperature comprised within the range of from 40° to 150° C.

In the preferred form of practical embodiment, the contact is carried out at temperatures comprised within the range of from 70° to 125° C., and at a pH value comprised within the range of from 4 to 6. The pH value is advantageously adjusted by means of the addition of an inorganic acid (e.g., sulphuric acid and phosphoric acid), or of an organic acid (e.g., formic acid and acetic acid).

The organic acid is advantageously used in an amount of the order of from 5 to 20% by weight in the solution of the ammonium salt. Particularly useful complexing agents for the process of the present invention are ammonium oxalate, ammonium citrate, ammonium acetate, ammonium sulphate and ammonium hydrogen phosphate.

The process of purification of the present invention is simply carried out by contacting oxamide powder, obtained by means of the Hoechst process, or of any other improved processes derived from the Hoechst process, and which uses copper-based catalysts (see, e.g., Chem. Abst. 84 89647, 85 93873, 123382 and 123383, 101 25378 and 40215), with the aqueous solution containing the complexating agent, according to one of the techniques commonly used for solid-liquid contact. Such an aqueous solution, which will generally contain percentages of the complexing agent comprised within the range of from 1% by weight up to the saturation value, will be used in such an amount as to contain a number of equivalents of complexing agent at least equal to the number of copper moles to be removed, but, preferably, an excess of said complexing agent.

The purification can be generally carried out at a temperature comprised within the range of from 40° to 150° C., and is preferably carried out at a temperature comprised within the range of from 70° to 125° C., by letting the oxamide to be purified stay in contact with the aqueous solution of the complexing agent for a time generally comprised within the range of from 0.5 to 6 hours, and preferably of from 0.5 to 3 hours. After this time has expired, the whole mass is cooled to room temperature, and oxamide is separated from the solution of the complexing agent containing the extracted copper, by means of any of the known operations of solid/liquid separation, such as filtration, decantation or centrifugation.

If a thorough purification of oxamide from copper is desired, such procedure can be repeated once or more times, every time, using a fresh solution of the complexating agent. On the other hand, it is possible as well, by using rather concentrated solutions of the complexing agent, to re-use such a solution coming from a purification step, for purifying another oxamide batch, until a critical copper concentration is reached, above which the extracting capacity of the solution decreases. Such an exhausted solution can be easily regenerated by means of special chemical treatments, and, essentially, via precipitation by chemical means, or by reduction to metal copper.

The purity degree of oxamide which can be obtained with the purification process according to the present invention depends on the solution of complexing agent which is used, on the weight ratio of complexing solution/oxamide, on the temperature, on the contact time, and on the number of the contact steps. For a better contact, it is furthermore recommended that an oxamide powder with a granulometry comprised within the range of from 300 to 3,000 meshes/$cm^2$ be used.

By means of the process of the present invention, a purified oxamide can be obtained, whose residual copper content is as low as 15 ppm.

The recovered amount of oxamide is of the order of from 96 to 98% of the charged amount, the losses being essentially a function of the temperature the treatment takes place at, which affects both the solubility of oxamide in water, and the kinetics of the transformation reaction; and of the pH value of the solution.

The following Examples, which illustrate, in greater detail, the process of the invention, with particular reference to the preferred aspects thereof, should anyway not be considered as being limitative of the purview of the same invention.

EXAMPLE 1

To an autoclave equipped with mechanical stirring means, and with a temperature control system, a solution of $(NH_4)_2C_2O_4$ at 4.2% w. in water (30 ml) and oxamide to be purified (3 g) - coming from the oxidation of HCN with oxygen in the presence of copper salts in $CH_3COOH/H_2O$, and containing 950 ppm of Cu - are charged.

The autoclave is heated to a temperature comprised within the range of from 100° to 120° C., and the contents thereof are kept stirred for a time interval of from 2 to 3 hours. The autoclave is then cooled to room temperature, and oxamide is centrifuged off from the liquid phase.

Oxamide is then washed once more with water (20 ml), and is centrifuged again, and the isolated oxamide is dried at 100° C., up to constant weight (2.9 g) (97% of charged oxamide).

On an aliquot of purified oxamide, the copper content is determined by means of an atomic absorption technique, with oxamide being preliminarily dissolved in sulphuric acid-nitric acid solution: 35 ppm of copper are found.

EXAMPLE 2

To the same equipment as described in Example 1, a saturated solution of $(NH_4)_2C_2O_4$ in water (30 ml), whose pH value is previously adjusted at 5 (from an initial pH value of 6.7) with $H_3PO_4$, and oxamide to be purified (3 g) are charged.

The autoclave is heated to 100° C., and the contents thereof are kept stirred for 3 hours; the autoclave is then cooled to room temperature.

After centrifugation, washing with water (20 ml), and drying at 100° C., 2.9 g of oxamide 97% of charged oxamide) is recovered.

By analysing, by means of an atomic absorption technique, the purified oxamide, after the preliminary dissolution thereof in sulphuric acid-nitric acid solution, 15 ppm of copper are found.

EXAMPLE 3

To the same equipment as described in Example 1, a solution of $(NH_4)_2SO_4$ at 30% in water (30 ml), and oxamide to be purified (3 g) are charged.

The autoclave is heated to 100° C., and the contents thereof are kept stirred at this temperature for 3 hours. The autoclave is then cooled to room temperature, and oxamide is centrifuged off from the liquid phase.

Oxamide is then washed with water (20 ml), and is centrifuged off once again; isolated oxamide is dried at 100° C. up to constant weight (2.94 g) (98% of charged oxamide).

On an aliquot of purified oxamide, the copper content is determined by means of an atomic absorption technique, after oxamide being preliminarily dissolved in sulphuric acid-nitric acid solution: 165 ppm of copper are found.

To the same equipment as previously described, the oxamide (2 g) obtained from the previous treatment, and a fresh solution of $(NH_4)_2SO_4$ at 30% in water (20 ml), are charged.

After heating and stirring at 100° C. for 3 hours, the separation and the washing of oxamide is carried out by centrifuging, with the same operating modalities as previously mentioned.

After drying, 1.96 g (98% of the charged oxamide) is recovered; the analysis, via atomic absorption, carried out on an aliquot of this oxamide, shows a content of 78 ppm of copper.

With a third treatment, in the same equipment, carried out on 1.5 g of oxamide obtained from the second step of purification, 1.47 g of oxamide containing 66 ppm of copper is recovered.

EXAMPLE 4

To the same equipment as described in Example 1, a solution of $(NH_4)_2SO_4$ at 30% in water (30 ml) is charged, to it 10% by weight of $CH_3COOH$, and oxamide to be purified (3 g) are added.

The autoclave is heated to 100° C., and the contents thereof are kept stirred at this temperature for 3 hours. The autoclave is then cooled to room temperature, and oxamide is centrifuged off from the liquid phase. Oxamide is then washed with water (20 ml), and is centrifuged again, with the separated oxamide being dried at 100° C., up to constant weight (2.9 g) (98% of charged oxamide).

On an aliquot of purified oxamide, the copper content is determined by means of an atomic absorption technique, with oxamide being preliminarily dissolved in sulphuric acid-nitric acid solution: 60 ppm of Cu are found.

EXAMPLE 5

To the same equipment as described in Example 1, a solution of $(NH_4)_2SO_4$ at 30% in water (30 ml), whose pH value is previously adjusted at 3 with $H_3PO_4$, and oxamide to be purified (3 g) are charged.

The autoclave is heated to 100° C., and the contents thereof are kept stirred for 3 hours. The autoclave is then cooled to room temperature, and oxamide is centrifuged off from the liquid phase.

Oxamide is then washed with water (20 ml) and is centrifuged again, and the separated oxamide is then dried at 100° C., up to the constant weight of 2.94 g (98% of charged oxamide).

On an aliquot of purified oxamide, the copper content is determined by means of an atomic absorption technique, with oxamide being preliminarily dissolved in sulphuric acid-nitric acid solution: 94 ppm of copper are found.

EXAMPLE 6

To the same equipment as described in Example 1, a solution of $CH_3COONH_4$ at 30% in water (30 ml), and oxamide to be purified (3 g) are charged.

The autoclave is heated to 100° C., and the contents thereof are kept stirred at this temperature for 3 hours.

The autoclave is then cooled down to room temperature, and oxamide is centrifuged off from the liquid phase.

Oxamide is then washed with water (20 ml) and is centrifuged again, and the separated oxamide is then dried at 100° C., up to constant weight (2.88 g) (96.3% of charged oxamide).

On an aliquot of purified oxamide, the copper content is determined by means of an atomic absorption technique, with oxamide being preliminarily dissolved in sulphuric acid-nitric acid solution: 98 ppm of copper are found.

EXAMPLE 7

To the same equipment as described in Example 1, a solution of ammonium citrate at 30% in water (30 ml), and oxamide to be purified (3 g) are charged.

The autoclave is heated to 100° C., and the contents thereof are kept stirred at this temperature for 3 hours. The autoclave is then cooled to room temperature, and oxamide is centrifuged off from the liquid phase.

Oxamide is then washed with water (20 ml) and is centrifuged again, and the separated oxamide is then dried at 100° C., up to constant weight (2.91 g) (97% of charged oxamide).

On an aliquot of purified oxamide, the copper content is determined by means of an atomic absorption technique, with oxamide being preliminarily dissolved in sulphuric acid-nitric acid solution: 89 ppm of copper are found.

EXAMPLE 8

To the same equipment as described in Example 1, a solution of $(NH_4)_2HPO_4$ at 30% in water, whose pH value is previously adjusted, from 8.6, to 5, by means of the addition of $H_3PO_4$, and oxamide to be purified (3 g) are charged.

The autoclave is heated to 100° C., and the contents thereof are kept stirred for 3 hours. The autoclave is then cooled to room temperature, and oxamide is centrifuged off from the liquid phase.

Oxamide is then washed with water (20 ml) and is centrifuged again, and the separated oxamide is then dried at 100° C., up to constant weight (2.93 g) (97.7% of charged oxamide).

On an aliquot of purified oxamide, the copper content is determined by means of an atomic absorption technique, with oxamide being preliminarily dissolved in sulphuric acid-nitric acid solution: 127 ppm of copper are found.

It should be observed that the same purification test, run according to similar modalities, under similar conditions, and by using similar ingredients, but without the preliminary correction of pH value (with $H_3PO_4$, from 8.6 to 5), yields, as the end product, an oxamide containing 52 ppm of copper (hence, with a better extraction capacity), but the lost amount of oxamide is of 20%; this demonstrates that the purification carried out at basic pH values favours more extensively the process of hydrolysis of the same oxamide.

We claim:

1. A process for removing copper form copper-containing oxamide comprising contacting said oxamide at least once with an effective amount of an aqueous solution of a complexing agent for copper comprising an ammonium salt of an organic or inorganic acid, wherein said copper and said complexing agent form a water-soluble copper complex, the process taking place at a pH form 2 to 8 and at a temperature from 40° to 150° C.

2. The process according to claim 1, wherein said complexing agent is selected from the group consisting of ammonium oxalate, ammonium citrate, ammonium acetate, ammonium sulfate and ammonium hydrogen phosphate.

3. The process according to claim 1, wherein said process is carried out at a pH of form 4 to 6 and at a temperature of form 70° to 125° C.

4. The process according to claim 1, wherein the pH value is adjusted by adding a mineral acid or an organic acid.

5. The process according to claim 4, wherein said pH adjusting acid is selected from the group consisting of sulfuric acid, phosphoric acid, formic acid and acetic acid.

6. The process according to claim 1, wherein said complexing agent is present in said aqueous solution at a concentration of from 1% by weight, up to the saturation value thereof.

7. The process according to claim 1, wherein the process is carried out with a contact time of from 0.5 to 6 hours.

8. The process according to claim 7, wherein the contact time is from 0.5 to 3 hours.

9. The process according to claim 1, wherein the step of contacting oxamide with said aqueous solution of said complexing agent is repeated one or more times.

10. The process according to claim 1, wherein said copper-containing oxamide has a particle size of from 300 to 3,000 mesh.

* * * * *